United States Patent [19]

Wood et al.

[11] Patent Number: 4,634,554

[45] Date of Patent: Jan. 6, 1987

[54] N-BENZYL,3-HYDROXYMETHYL AND 3-ALKANOYLOXYMETHYL AZETIDINE DERIVATIVES

[75] Inventors: Derek A. Wood, Sittingbourne; Ronald F. Mason, Ashford, both of England

[73] Assignee: Shell Oil Company, Houston, Tex.

[21] Appl. No.: 662,752

[22] Filed: Oct. 19, 1984

[30] Foreign Application Priority Data

Oct. 21, 1983 [GB] United Kingdom ............ 8328253

[51] Int. Cl.$^4$ .......................................... C07D 205/04
[52] U.S. Cl. .................................................. 548/950
[58] Field of Search ................................. 260/239 A

[56] References Cited

U.S. PATENT DOCUMENTS 4,201,774  5/1980  Igarashi et al. ............... 536/13.6 X
4,367,238  1/1983  Ueda et al. ........................ 514/450
4,544,751 10/1985  Takaya et al. ................. 548/204 X

FOREIGN PATENT DOCUMENTS 1169027 10/1969 United Kingdom .

OTHER PUBLICATIONS

Anderson, et al., J. Org. Chem., vol. 37(24), 1972, pp. 3953-3955.
Melloni, et al., J. Med. Chem., vol. 22(2), 1979, pp. 183-191.

Primary Examiner—Donald G. Daus
Assistant Examiner—William A. Teoli, Jr.

[57] ABSTRACT

Substituted azetidine derivatives of formula

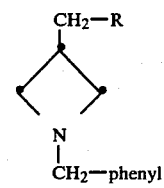

in which R represents chlorine, bromine, hydroxy or alkanoyloxy of up to 6 carbon atoms, processes for their preparation and their use as intermediates for the preparation of azetidine-3-carboxylic acid.

2 Claims, No Drawings

N-BENZYL,3-HYDROXYMETHYL AND 3-ALKANOYLOXYMETHYL AZETIDINE DERIVATIVES

BACKGROUND OF THE INVENTION

Azetidine-3-carboxylic acid

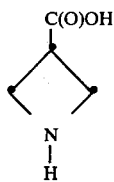

is of interest as a chemical hybridizing agent, inasmuch as it sterilizes the male parts of plants without significant adverse effect upon the female parts of those plants.

It is desirable that a method for the preparation of that compound be available.

DESCRIPTION OF THE INVENTION

It now has been found that azetidine-3-carboxylic acid can be prepared by the following sequence of reactions:

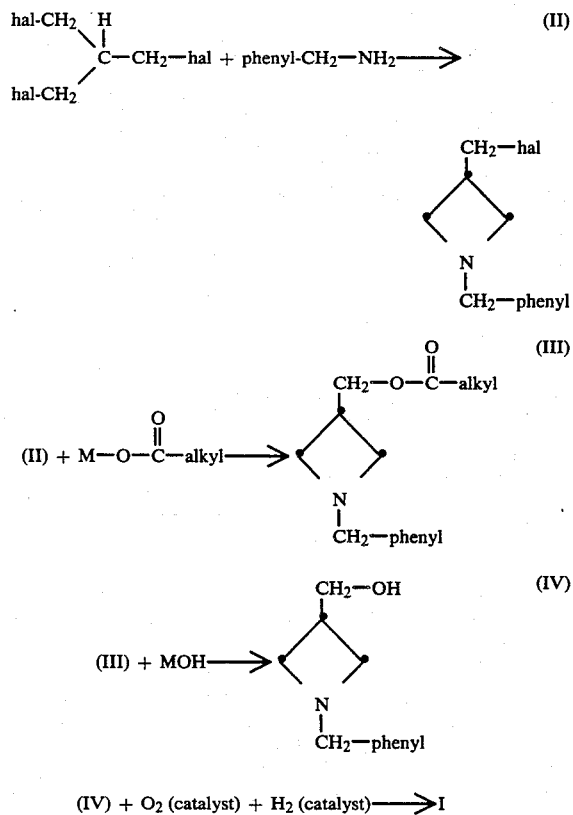

In these compounds, each hal represents chlorine or bromine, the alkyl moiety contains up to five carbon atoms and M represents an alkali metal. Chlorine is the preferred halogen, methyl is the preferred alkyl moiety and sodium is the preferred alkali metal.

The intermediate II is prepared by treating the trihalobutane with benzylamine in the presence of an alkali metal hydroxide, preferably sodium hydroxide, in a hydrocarbon solvent, such as petroleum ether, at a temperature of from about 50° C. to about 100° C.

The intermediate III is prepared by treating the intermediate II with the alkali metal alkanoate, in a non-aqueous polar solvent, such as dimethylformamide, at a temperature of from about 100° C. to about 150° C.

The intermediate IV is prepared by treating the intermediate III with the alkali metal hydroxide in an aqueous alkanol, such as methanol, at or somewhat above room temperature.

The intermediate IV is converted to the product I by conventional catalytic oxidation, followed by conventional hydrogenolysis.

In each of the process steps, the product is recovered and isolated by conventional procedures, as illustrated in the following examples.

EXAMPLE 1

1-benzyl-3-chloromethyl azetidine (1)

A mixture of 2813 g of 2-(chloromethyl)-3-chloro-prop-1-ene and 31 g of tertiary-butyl peroxide was stirred at 45°-55° C. while 2238 g of gaseous hydrogen bromide was added over 7 hours. The resulting mixture was washed with water and distilled under reduced pressure to give 1-bromo-2-(chloromethyl)-3-chloropropane (1A), as a colorless liquid, b.p.: 60°-70° C., 0.2-0.5 Torr.

59 g of benzylamine was added drop-by-drop over two hours to a stirred, refluxing mixture of 103 g of 1A, 50 ml of water and 200 ml of 100°/120° C. petroleum ether, under nitrogen, at 80° C., the pH of the mixture being maintained at 7-7.5. A solution of 40 g of sodium hydroxide in 60 ml of water was then added slowly to the stirred, refluxing mixture, at a rate sufficient to maintain the pH of the mixture at about 8. The resulting mixture was cooled and the aqueous phase was removed. The organic phase was washed with water, the solvent was evaporated under reduced pressure, and the residue was distilled in a wiped-film evaporator to give 1, as a colorless oil, b.p.: 80° C., 0.01 Torr.

Example 2

1-benzyl-3-(acetoxymethyl)-azetidine (2)

195.5 g of 1 was added, drop-by-drop over 45 minutes, to a stirred mixture of 164 g of anhydrous sodium acetate and 1.8 liters of dimethylformamide, at 130° C. The mixture was held at 130° C. for an additional 2.25 hours, then most of the solvent was evaporated under reduced pressure and the cooled residue and treated with sufficient of an ice/water mixture to dissolve the salts therein. The resulting mixture was extracted with ether, the extract was washed with water, and the solvent was evaporated to give 2, as a pale yellow oil, b.p.: 94° C., 0.1 Torr.

EXAMPLE 3

1-benzyl-3-hydroxymethylacetidine (3)

A mixture of 191 g of 2, 1.2 liters of ethanol and 65 g of potassium hydroxide, as an 85% aqueous solution, was held at room temperature for 16 hours, then the solvent was evaporated under reduced pressure. The residue was dissolved in a small amount of water and the solution was extracted with ether. The solvent was evaporated from the extract under reduced pressure and the residue was distilled in a wiped-film evaporator, to give 3, as a pale yellow oil, b.p.: 90° C., 0.02 Torr.

EXAMPLE 4

Compound (I)

A mixture of 17.7 g of 3, 4.0 g of sodium hydroxide, 350 ml of water and 7.0 g of a 5% platinum-on-charcoal catalyst was stirred at 80° C. while a stream of oxygen was passed into the mixture for 2 hours. The cooled mixture was filtered, and the water evaporated under reduced pressure. The residue was dissolved in 100 ml of acetic acid and hydrogenated in the presence of 2.4 g of 5% palladium-on-carbon catalyst. The resulting mixture was filtered, and the solvent was evaporated from the filtrate. The residue was dissolved in water and passed down a column of Dowex 50H form ion exchange resin, using 2M aqueous ammonium hydroxide solution as eluent. The eluent was evaporated from the fractions giving a positive ninhydrin test, to give I, as a white crystalline solid, m.p.: 285°–290° C., with decomposition.

We claim:

1. A compound of the formula

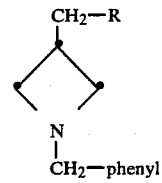

wherein R is hydroxy or alkanoyloxy of two to six carbon atoms.

2. A compound according to claim 1 wherein the alkanoyloxy moiety is acetoxy.

* * * * *